(12) United States Patent
Nara

(10) Patent No.: US 10,813,542 B2
(45) Date of Patent: Oct. 27, 2020

(54) IMAGE PICKUP APPARATUS FOR ENDOSCOPE

(71) Applicant: OLYMPUS CORPORATION, Tokyo (JP)

(72) Inventor: Tetsuro Nara, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 455 days.

(21) Appl. No.: 15/788,355

(22) Filed: Oct. 19, 2017

(65) Prior Publication Data

US 2018/0035878 A1 Feb. 8, 2018

Related U.S. Application Data

(63) Continuation of application No. PCT/JP2016/082325, filed on Oct. 31, 2016.

(30) Foreign Application Priority Data

Feb. 2, 2016 (JP) .................................. 2016-018119

(51) Int. Cl.
*A61B 1/05* (2006.01)
*A61B 1/04* (2006.01)
(Continued)

(52) U.S. Cl.
CPC .............. *A61B 1/05* (2013.01); *A61B 1/0011* (2013.01); *A61B 1/042* (2013.01); *A61B 1/045* (2013.01);
(Continued)

(58) Field of Classification Search
CPC ....... A61B 1/0011; A61B 1/042; A61B 1/045; A61B 1/128; G02B 23/2484; G03B 17/55
See application file for complete search history.

(56) References Cited

U.S. PATENT DOCUMENTS 3,579,269 A * 5/1971 Ostensen ........... A61B 1/00032
362/158
3,592,199 A * 7/1971 Ostensen ............... A61B 1/267
600/198

(Continued)

FOREIGN PATENT DOCUMENTS

EP 0 978 251 A1 2/2000
JP H07100104 A 4/1995
(Continued)

OTHER PUBLICATIONS

Extended Supplementary European Search Report dated Jan. 21, 2019 in European Patent Application No. 16 88 9367.5.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An image pickup apparatus for an endoscope includes an exterior member; an internal unit including an image pickup unit; a fixing frame formed of metal and including at least one fixing portion configured to retain the internal unit and to fix the internal unit to an inner surface of the exterior member; and a washer provided between the at least one fixing portion and a screw hole of the inner surface, the washer being formed of a member with a lower thermal conductivity than metal, wherein the at least one fixing portion of the retaining member is fixed to the fixing part of the exterior member by a fixing member via the heat insulating member, and the heat insulating member covers an outer circumference of the fixing member.

12 Claims, 10 Drawing Sheets

(51) Int. Cl.
*A61B 1/00* (2006.01)
*G02B 23/24* (2006.01)
*A61B 1/12* (2006.01)
*A61B 1/045* (2006.01)
*G03B 17/55* (2006.01)
*H04N 5/225* (2006.01)

(52) U.S. Cl.
CPC .......... *A61B 1/128* (2013.01); *G02B 23/2484* (2013.01); *G03B 17/55* (2013.01); *H04N 5/2256* (2013.01); *H04N 2005/2255* (2013.01)

(56) References Cited

U.S. PATENT DOCUMENTS

| | | | | | |
|---|---|---|---|---|---|
| 3,876,967 | A | * | 4/1975 | Hehl | H01C 10/30 338/126 |
| 5,609,561 | A | * | 3/1997 | Uehara | A61B 1/042 348/75 |
| 5,653,672 | A | * | 8/1997 | Niinai | B04B 15/02 494/14 |
| 6,073,449 | A | * | 6/2000 | Watanabe | H01L 35/30 62/3.2 |
| 6,080,101 | A | * | 6/2000 | Tatsuno | A61B 1/00124 348/65 |
| 6,547,721 | B1 | * | 4/2003 | Higuma | A61L 2/07 600/133 |
| 6,572,537 | B2 | | 6/2003 | Futatsugi et al. | |
| 7,435,215 | B2 | * | 10/2008 | Seto | A61B 1/0051 600/106 |
| 2001/0016679 | A1 | * | 8/2001 | Futatsugi | A61B 1/05 600/133 |
| 2016/0278623 | A1 | * | 9/2016 | Hirata | G02B 23/24 |

FOREIGN PATENT DOCUMENTS

| | | |
|---|---|---|
| JP | 2013056003 A | 3/2013 |
| JP | 2015132795 A | 7/2015 |
| WO | 2015087570 A1 | 6/2015 |

OTHER PUBLICATIONS

International Search Report dated Jan. 24, 2017 issued in PCT/JP2016/082325.

\* cited by examiner

IMAGE PICKUP APPARATUS FOR ENDOSCOPE

CROSS REFERENCE TO RELATED APPLICATION

This application is a continuation application of PCT/JP2016/082325 filed on Oct. 31, 2016 and claims benefit of Japanese Application No. 2016-018119 filed in Japan on Feb. 2, 2016, the entire contents of which are incorporated herein by this reference.

BACKGROUND OF THE INVENTION

1. Field of the Invention

The present invention relates to an image pickup apparatus for an endoscope, the image pickup apparatus including an exterior member which maintains an internal portion in an airtight manner and which is configured of one-layer metal.

2. Description of the Related Art

An image pickup apparatus for an endoscope is configured to pick up an image of an examination portion inside a subject and output the picked-up image of the examination portion to a monitor, and for example, a configuration allowing connection to an eyepiece section (hereinafter referred to as an eyepiece) provided on a proximal end side of an insertion section of an endoscope is well known.

The image pickup apparatus for an endoscope has to be reliably cleaned, disinfected and sterilized after use. As a method for sterilizing the image pickup apparatus for an endoscope, high-temperature high-pressure steam sterilization process (hereinafter referred to as "autoclave process") for performing sterilization using high-temperature high-pressure steam is well known.

Normally, an internal unit including an image pickup unit configured of an image pickup device, an objective optical system and the like of the image pickup apparatus for an endoscope is provided inside an exterior member of the image pickup apparatus for an endoscope, but high-temperature high-pressure steam enters the exterior member in the autoclave process.

At this time, because the image pickup device breaks down or the objective optical system is clouded when the image pickup unit comes into contact with the high-temperature high-pressure steam, the image pickup unit has to be provided at a position, inside the exterior member, where the high-temperature high-pressure steam does not enter.

According to Japanese Patent Application Laid-Open Publication No. 2013-56003, with respect to an image pickup apparatus for an endoscope, which is attached to an eyepiece section of an endoscope, an airtight case formed of resin is provided inside an exterior member formed of metal such as stainless steel, and an internal unit including an image pickup unit is sealed inside the airtight case. A configuration of an image pickup apparatus for an endoscope, configured to protect an image pickup unit from high-temperature high-pressure steam entering an exterior member is thus disclosed.

Now, in the case where the exterior member is formed of one layer, a configuration is conceivable according to which at least one fixing portion of a retaining member which is configured to retain the internal unit and which is formed of metal is fixed to a fixing part, such as a screw hole, provided on an inner surface of the internal unit by a fixing member such as a screw.

Note that the internal unit is directly fixed to an inner surface of the exterior member because the internal unit has to be accurately positioned and fixed inside the exterior member so as to enhance an optical characteristics of an objective optical system provided in the internal unit.

Moreover, the retaining member is formed of metal for the following reason. The image pickup device of the internal unit is a heat generating element that generates heat when driven. Accordingly, when the image pickup device is driven, the temperature inside the exterior member having the airtight structure is increased due to the heat from the image pickup device. Thus, to prevent the image pickup device from breaking down due to the increase in the temperature, the heat from the image pickup device has to be transferred to the exterior member via the retaining member, and has to be discharged outside the exterior member.

SUMMARY OF THE INVENTION

An image pickup apparatus for an endoscope according to an aspect of the present invention includes an exterior member configured to maintain an internal portion in an airtight manner, the exterior member being formed of one-layer metal; an internal unit provided in the internal portion of the exterior member, the internal unit including a heat generating element; a retaining member provided in the internal unit, the retaining member being formed of metal and including at least one fixing portion configured to retain the internal unit and to fix the internal unit to an inner surface of the exterior member; and a heat insulating member provided between the at least one fixing portion of the retaining member and a fixing part of the inner surface of the exterior member, the heat insulating member being formed of a member with a lower thermal conductivity than metal, wherein the at least one fixing portion of the retaining member is fixed to the fixing part of the exterior member by a fixing member via the heat insulating member, and the heat insulating member covers an outer circumference of the fixing member.

Furthermore, an image pickup apparatus for an endoscope according to another aspect of the present invention includes an exterior member configured to maintain an internal portion in an airtight manner, the exterior member being formed of one-layer metal; an internal unit provided in the internal portion of the exterior member, the internal unit including a heat generating element; a retaining member provided in the internal unit, the retaining member being formed of metal and including at least one fixing portion configured to retain the internal unit and to fix the internal unit to an inner surface of the exterior member; and a heat insulating member provided between the at least one fixing portion of the retaining member and a fixing part of the inner surface of the exterior member, the heat insulating member being formed of a member with a lower thermal conductivity than metal, wherein the retaining member is configured such that a part of the retaining member is connected to a metal provided in a region covered by the member with a lower thermal conductivity than metal.

DETAILED DESCRIPTION OF THE PREFERRED EMBODIMENT(S)

Hereinafter, an embodiment of the present invention will be described with reference to the drawings. Note that the drawings are schematic, and the relationship between a thickness and a width of each member, the ratio of thicknesses of members and the like are not actual, and it is needless to say that the relationship between dimensions and the ratios may be different between the drawings.

Figure 1:
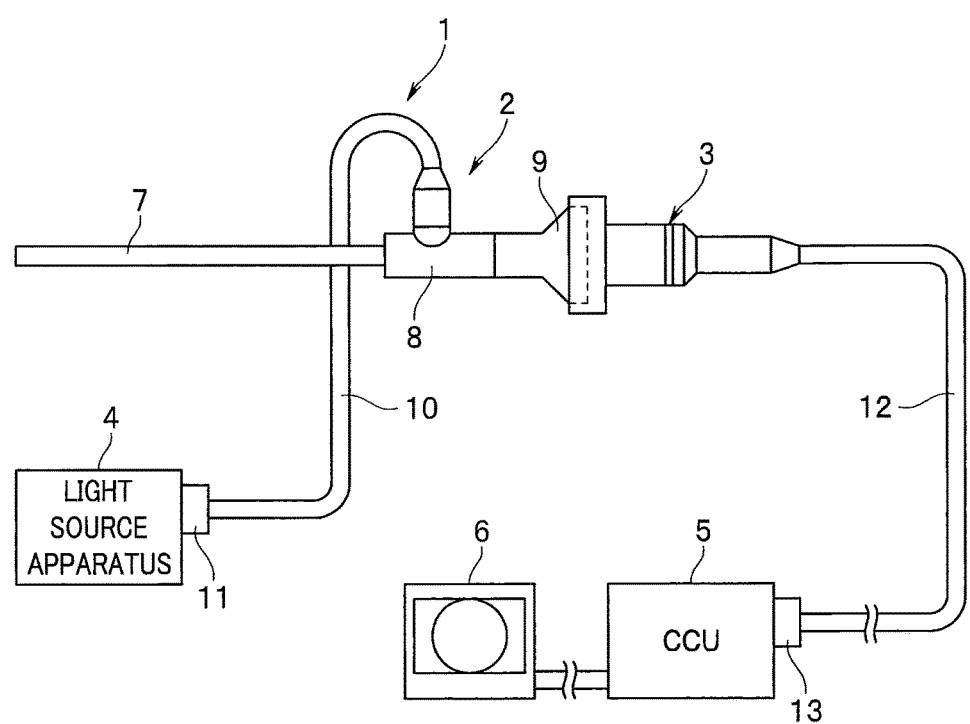
FIG. 1 is a diagram schematically showing a configuration of an endoscope system provided with an image pickup apparatus for an endoscope, according to an embodiment of the present invention.

FIG. 1 is a diagram schematically showing a configuration of an endoscope system provided with an image pickup apparatus for an endoscope, according to a present embodiment.

As shown in FIG. 1, an endoscope system 1 includes an endoscope 2, a camera head 3 as an image pickup apparatus for an endoscope, that can be detachably connected to the endoscope 2, and a light source apparatus 4 configured to supply illumination light to the endoscope 2.

Furthermore, the endoscope system 1 includes a camera control unit (CCU) 5 configured to perform signal processing and the like on an image pickup signal from the camera head 3, and a monitor 6 configured to display a video signal that is outputted from the CCU 5.

Main sections of the endoscope 2 are configured of an elongated insertion section 7, a grasping section 8 that is provided on a proximal end side of the insertion section 7 and that has a larger diameter than the insertion section 7, and an eyepiece 9 that is provided on a proximal end of the grasping section 8.

Moreover, one end of a light guide cable 10, the other end of which is detachably attached to the light source apparatus 4 by a connector 11, is detachably connected to a pipe sleeve which is provided at a side portion of the grasping section 8 of the endoscope 2.

Accordingly, light that is emitted from a lamp, not shown, inside the light source apparatus 4 is supplied to the endoscope 2 via the light guide cable 10, and illuminates the inside of a subject through an illumination window, not shown, which is provided at a distal end of the insertion section 7.

An image of the inside of the subject illuminated by the illumination light is formed as an optical image on an objective optical system, not shown, provided at the distal end of the insertion section 7, and the optical image that is formed enters a lens provided inside the eyepiece 9 through a relay lens or the like, not shown, provided inside the insertion section 7. An operator is thus enabled to observe the optical image through the eyepiece 9.

Furthermore, as described above, the camera head 3 is detachably connected to the eyepiece 9 of the endoscope 2. A camera cable 12 extends from the camera head 3, and an extended end of the camera cable 12 is detachably attached to the CCU 5 by a connector 13 provided at the extended end.

The CCU 5 is configured to generate an image signal based on an image pickup signal transmitted from the camera head 3 through the camera cable 12, and to cause an image of the inside of the subject to be displayed on the monitor 6 as an endoscopic image.

Figure 2:
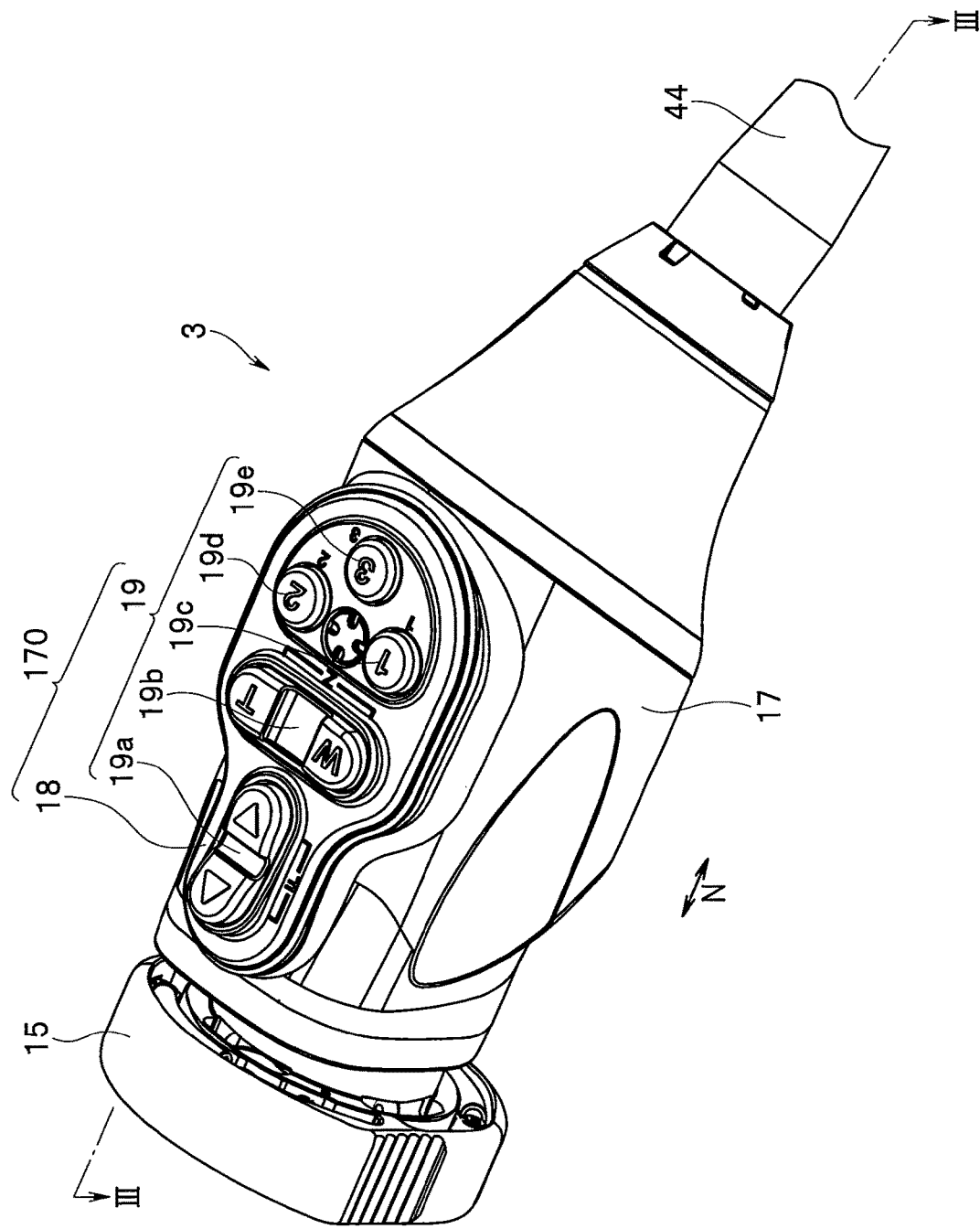
FIG. 2 is a perspective view showing a camera head in FIG. 1.
Figure 4:
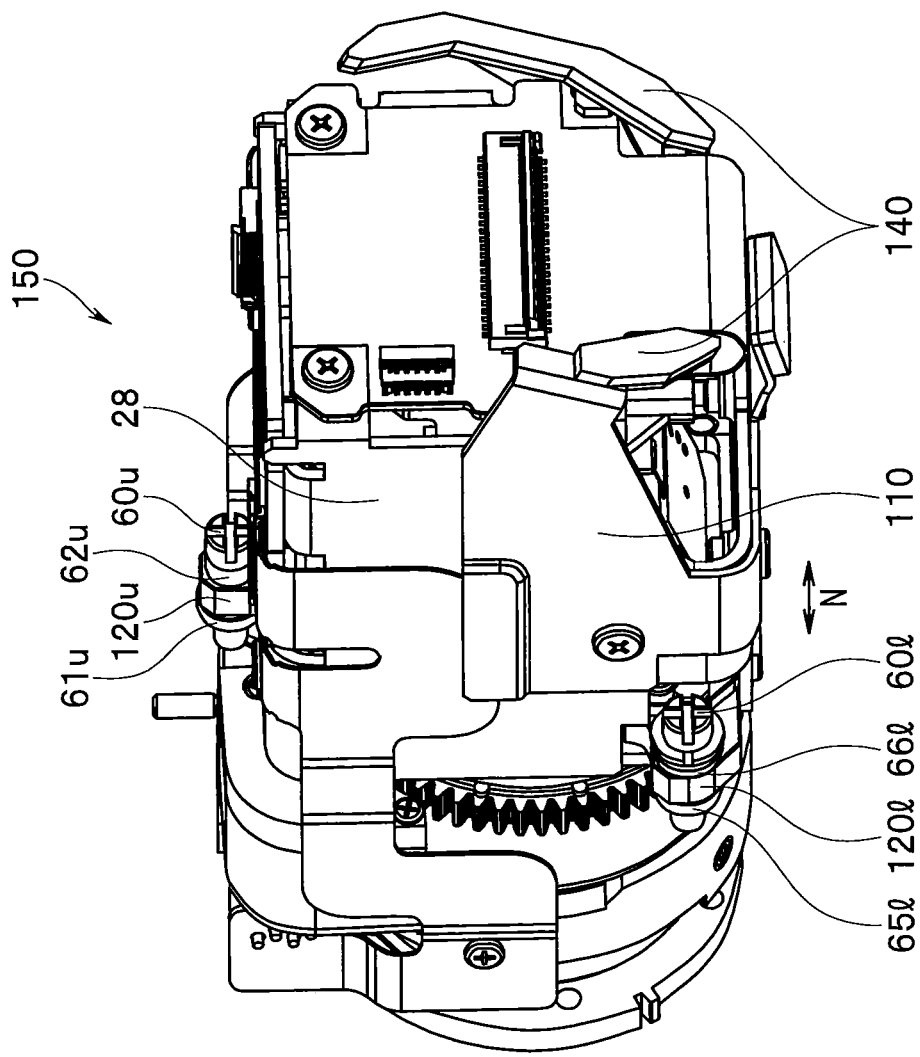
FIG. 4 is a perspective view showing an internal unit in FIG. 3.
Figure 5:
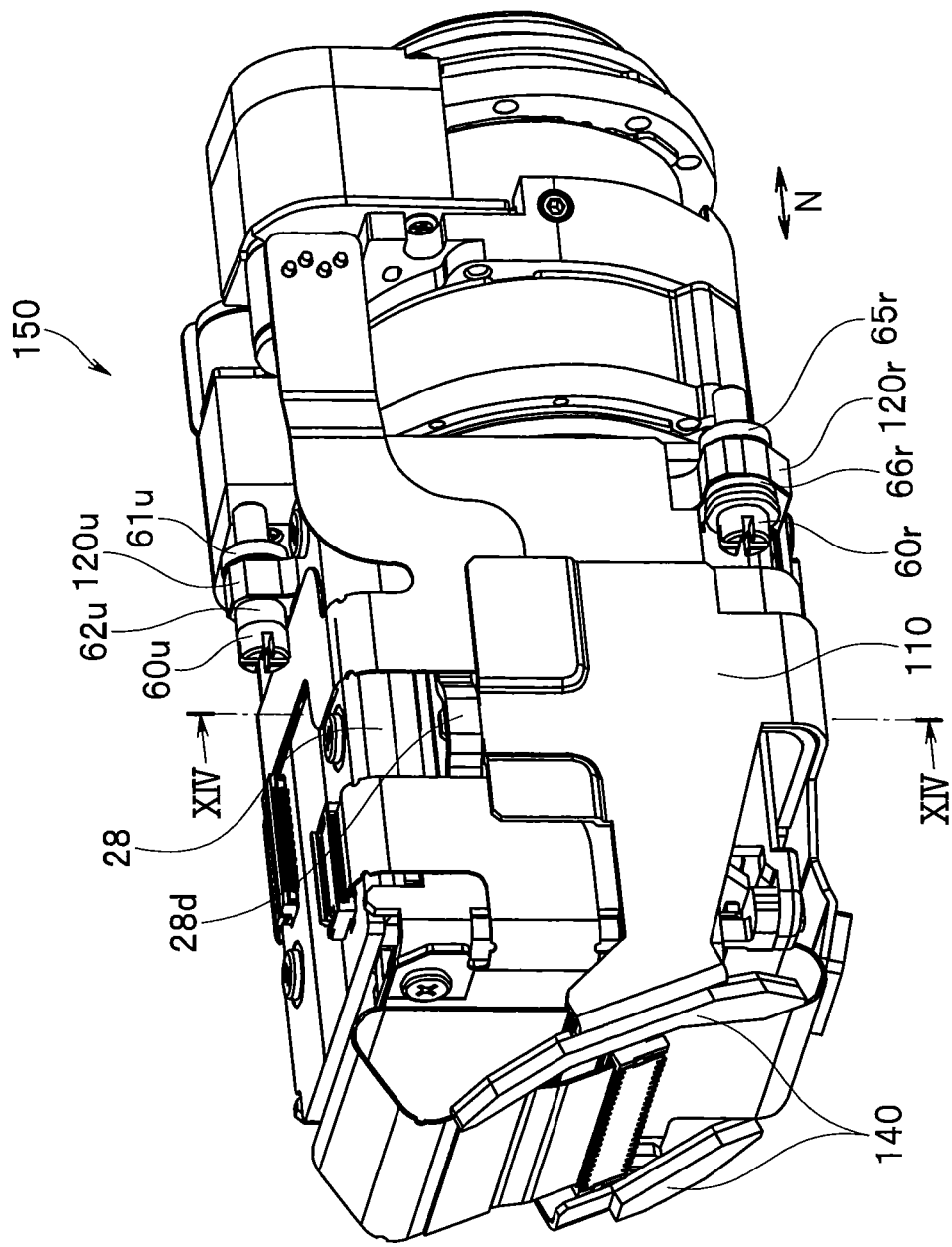
FIG. 5 is a perspective view showing the internal unit in FIG. 3 from a different direction from FIG. 4.

Next, a specific configuration of the camera head 3 described above will be described with reference to FIGS. 2 to 5. FIG. 2 is a perspective view showing the camera head in FIG. 1, FIG. 3 is a partial cross-sectional view of the camera head taken along line III-III in FIG. 2, FIG. 4 is a perspective view showing an internal unit in FIG. 3, and FIG. 5 is a perspective view showing the internal unit in FIG. 3 from a different direction from FIG. 4.

Figure 3:
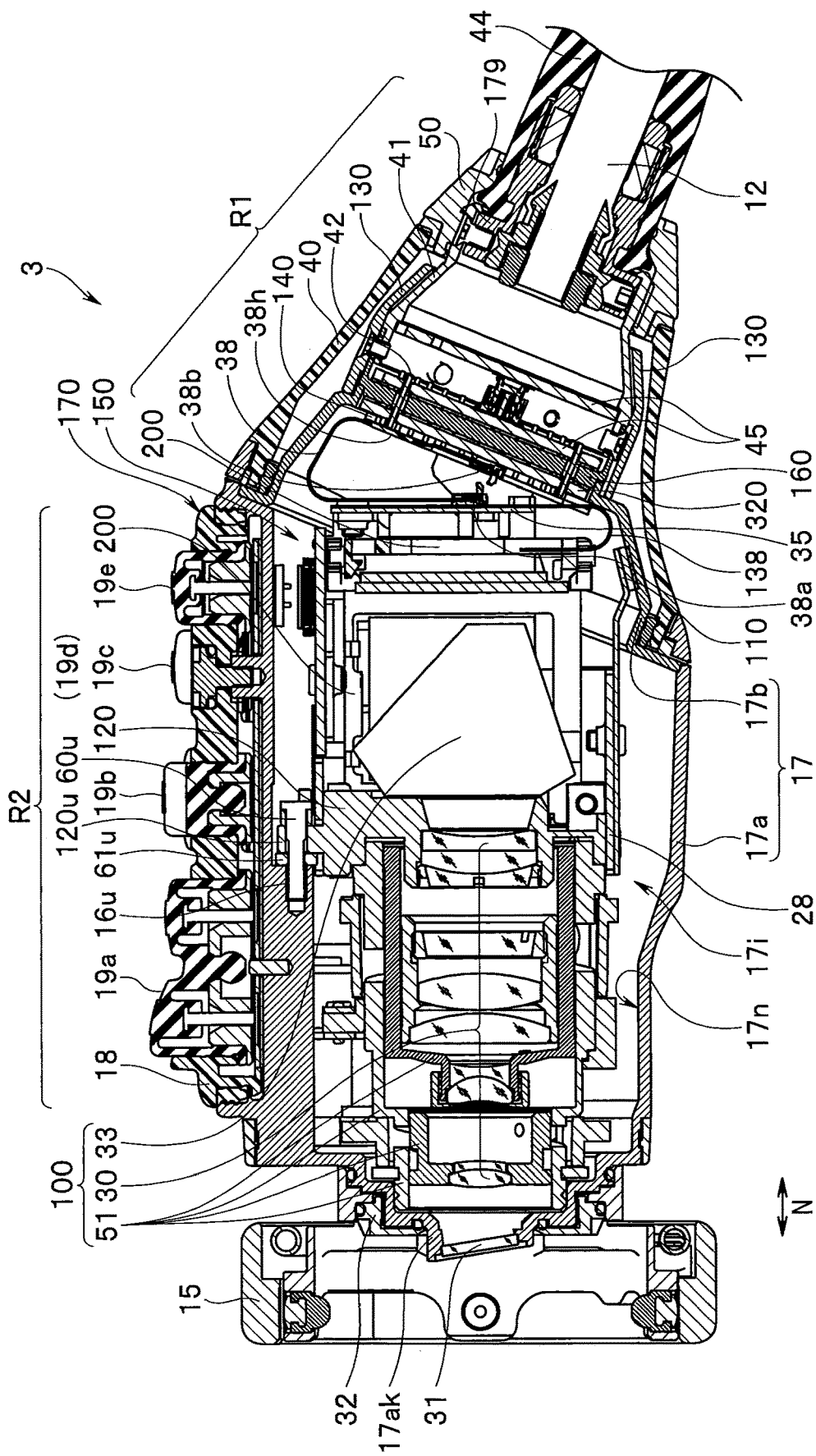
FIG. 3 is a partial cross-sectional view of the camera head taken along line III-III in FIG. 2.

As shown in FIGS. 2 and 3, main sections of the camera head 3 are configured of a coupler portion 15, and an exterior member 17, a distal end of which is fixed to the coupler portion 15.

As shown in FIG. 3, the coupler portion 15 is a member to which the eyepiece 9 of the endoscope 2 is connected, and is fixed to an outer circumference of on a distal end 17ak side of the exterior member 17 by using fixing screws 32.

The exterior member 17 maintains an internal portion in an airtight manner, is formed of one-layer metal, and is configured of a main cover 17a and a rear cover 17b, which is fixed to a proximal end of the main cover 17a in a liquid-tight and airtight manner by soldering, welding or the like. That is, the exterior member 17 serves also as an airtight case.

Note that to reduce the weight, titanium is cited as the metal for forming the exterior member 17, for example.

Also, as the metal for forming the exterior member 17, a metal which is light and which has a low thermal conductivity is desirable. However, any metal, such as stainless steel, may be used if the metal allows airtight welding which prevents high-temperature high-pressure steam from entering an internal portion 17i during the autoclave process described above.

Moreover, as shown in FIGS. 2 and 3, a switch unit 170 used for an image pickup operation for an image of the inside of a subject is fixed, along a longitudinal direction N of the camera head 3, to one side of the main cover 17a, or more specifically, on an outer circumferential side surface on an upper part as shown in FIGS. 2 and 3.

The switch unit 170 includes a plurality of switch buttons 19 covered with rubber covers or the like, and a switch button frame 18 that attaches the plurality of switch buttons 19 to the main cover 17a in a liquid-tight manner.

The plurality of switch buttons 19 include a focus adjustment button 19a configured to perform focus adjustment by moving a part of a lens 30, described below (see FIG. 3), forward or backward, a zoom button 19b configured to adjust focal magnification by moving a part of the lens 30 forward or backward, a brightness adjustment button 19c, a color adjustment button 19d, a release button 19e, and the like.

Furthermore, the switch button frame 18 is formed of a member with a lower thermal conductivity than metal, such as a resin material, and covers an upper portion of the main cover 17a along the longitudinal direction N.

Moreover, as shown in FIG. 3, an internal unit 150, shown in FIGS. 3 to 5, including an image pickup unit 100, which is a heat generating element, is provided inside the internal portion 17i that is hermetically sealed by the exterior member 17.

Note that at the time of assembly, the internal unit 150 is inserted into the internal portion 17i from a rear opening of the main cover 17a of the exterior member 17 in a state where the rear cover 17b is not fixed to the main cover 17a.

In the present configuration, the main cover 17a is configured of one component. Accordingly, compared to a case where a plurality of components are used, a configuration of abutting and fixing each fixing portion 120u, 120r, 120l of a fixing frame 120 of the internal unit 150 to a fixing part of the exterior member 17 described below enables the positioning accuracy of the internal unit 150 to be increased, and optical eccentricity of the lens 30 and the like may be prevented.

Main sections of the image pickup unit 100 are configured of a plurality of lenses 30, a lens frame 51 configured to retain the lenses 30, an image pickup device 33, and electrical components such as various substrates.

More specifically, as shown in FIG. 3, the plurality of lenses 30 are positioned along the longitudinal direction N and facing an observation window 31, which is hermetically fixed inside the distal end 17ak of the main cover 17a by soldering or the like by having an outer circumference metallized.

Note that when the eyepiece 9 of the endoscope 2 is connected to the coupler portion 15 of the camera head 3, the observation window 31 is positioned facing a lens in the eyepiece 9 along the longitudinal direction N.

Also, in the internal portion 17i of the exterior member 17, the plurality of lenses 30 retained by the lens frame 51 are provided behind the observation window 31, and the image pickup device 33 is positioned at an image formation position of the plurality of lenses 30.

Note that the lens frame 51 and the image pickup device 33 are retained by the fixing frame 120, which is a retaining member that is provided between the lens frame 51 and the image pickup device 33 along the longitudinal direction N.

The fixing frame 120 is for retaining the internal unit 150, and is formed of metal so as to discharge heat from the image pickup device 33.

Furthermore, as shown in FIGS. 3 to 5, the fixing frame 120 includes fixing portions 120u, 120r, 120l configured to fix the internal unit 150 to an inner surface 17n of the main cover 17a.

Note that as shown in FIGS. 4 and 5, the fixing portion 120u is provided at an upper side in the drawings, the fixing portion 120r is provided on a right side on a lower side in the drawings when the observation window 31 is at the front, and the fixing portion 120l is provided on a left side on the lower side in the drawings when the observation window 31 is at the front.

More specifically, the fixing portions 120u, 120r, 120l are provided about every 120 degrees in a circumferential direction of the internal unit 150.

Note that the fixing portions of the fixing frame 120 may be provided in plurality other than three, or the number of fixing portions may be one. Also, the configuration of fixation to the inner surface 17n using the fixing portions 120u, 120r, 120l of the fixing frame 120 will be described below.

Furthermore, in the following, the fixing portion 120u will be referred to as an upper-side fixing portion 120u, and the fixing portions 120r, 120l will be referred to as lower-side fixing portions 120r, 120l.

Moreover, as shown in FIG. 3, the internal unit 150 is provided in the internal portion 17i of the exterior member 17 without coming into contact with the inner surface 17n except at the fixing portions 120u, 120r, 120l of the fixing frame 120 and a heat dissipation sheet 140 that is described below.

Furthermore, as shown in FIG. 3, various substrates which are retained by a substrate holder 200, which is bent into an L shape, and which are electrically connected to the image pickup device 33 are provided in the internal portion 17i of the exterior member 17, behind the image pickup device 33.

Various substrates are electrically connected to a substrate 35 positioned behind the substrate holder 200 by a flexible substrate 138, which is bent into a U shape.

The substrate holder 200 and the substrate 35 are fixed to a frame 28, which is fixed to an outer circumference of the fixing frame 120.

A connector 38a of a flexible substrate 38, which is bent into a U shape that is vertically inverted from the flexible substrate 138 and which extends from the substrate 35, is electrically connected to the substrate 35.

Also, a connector 38b that is provided at an extended end of the flexible substrate 38 is electrically connected to a substrate 320, which is provided in an inclined manner behind the substrate 35.

A hermetic connector 160, which is fixed to the inner surface 17n on an end portion of the rear cover 17b by welding or the like, is provided on a proximal end side of the substrate 320, and a substrate 45 is provided on a proximal end side of the hermetic connector 160.

A plurality of conductive pins 42, which penetrate the hermetic connector 160, are provided in the hermetic connector 160, and the substrate 320 and the substrate 45 are electrically connected by the conductive pins 42.

Moreover, as shown in FIG. 3, a distal end of a cable fixing frame 41, which is a metal pipe sleeve, is connected to a proximal end side of the rear cover 17b via the hermetic connector 160.

Note that an outer circumference of the proximal end side of the rear cover 17b, an outer circumference of the hermetic connector 160, and an outer circumference of a distal end side of the cable fixing frame 41 are covered with a heat sink 130, which is an outer-exterior member heat transfer member which is formed of metal. Note that the heat sink 130 is formed of a material, such as a copper material, that has a higher thermal conductivity than the rear cover 17*b*, which is formed of titanium.

Moreover, a spacer ring 179 is fixed to a proximal end of the cable fixing frame 41, and a distal end of the camera cable 12 is connected to an inner circumferential surface of the spacer ring 179.

A plurality of electrical cords provided on outer circumferences of metal conductors and formed of member of resin material, for example, with a lower thermal conductivity than the metal are housed inside the camera cable 12, and distal ends of the electrical cords are extended into the cable fixing frame 41 and are electrically connected to the substrate 45.

Furthermore, an outer circumferential surface of the camera cable 12 is covered by a bend preventing portion 44 configured to prevent drastic bending of the camera cable 12.

Also, a rear screw 50 movably covers an outer circumference of the bend preventing portion 44, and a distal end side of the camera cable 12 is fixed to the cable fixing frame 41 by the rear screw 50 in a liquid-tight and airtight manner.

Moreover, an exterior cover 40 formed of a member with a lower thermal conductivity than metal, such as a member of a resin material such as Radel (registered mark) or PEEK, is provided to cover from a distal end of the rear cover 17*b* to a distal end of the rear screw 50 to cover an outer circumference of the rear cover 17*b*, an outer circumference of the heat sink 130, and an outer circumference of a proximal end side of the cable fixing frame 41.

A heat dissipation plate 110, which is an inner-exterior member heat transfer member extending from the fixing frame 120 to a region R1 covered by the exterior cover 40 in the internal portion 17*i* of the exterior member 17, is fixed to the fixing frame 120. Note that the heat dissipation plate 110 is formed of metal.

That is, as shown in FIGS. 3 to 5, the heat dissipation plate 110, having a angled-U shape that is opened upward in the drawings, extends rearward from the fixing frame 120 to an inside of the rear cover 17*b* along an outer circumferential surface of the frame 28.

Note that because the heat dissipation plate 110 is connected to the fixing frame 120 formed of metal, heat that is transferred from the image pickup device 33 to the fixing frame 120 is further transferred to a rear side of the internal unit 150.

Moreover, as shown in FIGS. 3 to 5, the heat dissipation sheet 140 formed of a rubber (gel) sheet having a relatively high thermal conductivity is provided on a proximal end surface of the heat dissipation plate 110 while being in surface contact with the inner surface 17*n* of the rear cover 17*b* in a state of being squashed by the inner surface 17*n*. Heat from the heat dissipation sheet 140 is thereby reliably transferred to the rear cover 17*b*.

Accordingly, heat transferred from the image pickup device 33 to the fixing frame 120 is transferred to the heat sink 130 via the heat dissipation plate 110, the heat dissipation sheet 140, and the rear cover 17*b*, and is then transferred to the conductor of the camera cable 12 via the cable fixing frame 41.

That is, the heat is transferred to the region R1 covered by the exterior cover 40, and is then transferred to the camera cable 12. Note that as described above, the heat sink 130 is formed of metal with a higher thermal conductivity than the rear cover 17*b*, and thus, heat from the rear cover 17*b* is efficiently transferred to the heat sink 130 without being emitted outside.

The exterior cover 40 prevents heat from being directly discharged outside from the rear cover 17*b*, the heat sink 130, and the cable fixing frame 41, which are formed of metal respectively, by covering the outer circumference of the rear cover 17*b*, the outer circumference of the heat sink 130, and the outer circumference of the proximal end side of the cable fixing frame 41. In other words, the exterior cover 40 prevents an operator from directly touching the rear cover 17*b*, the heat sink 130, and the cable fixing frame 41.

Figure 6:
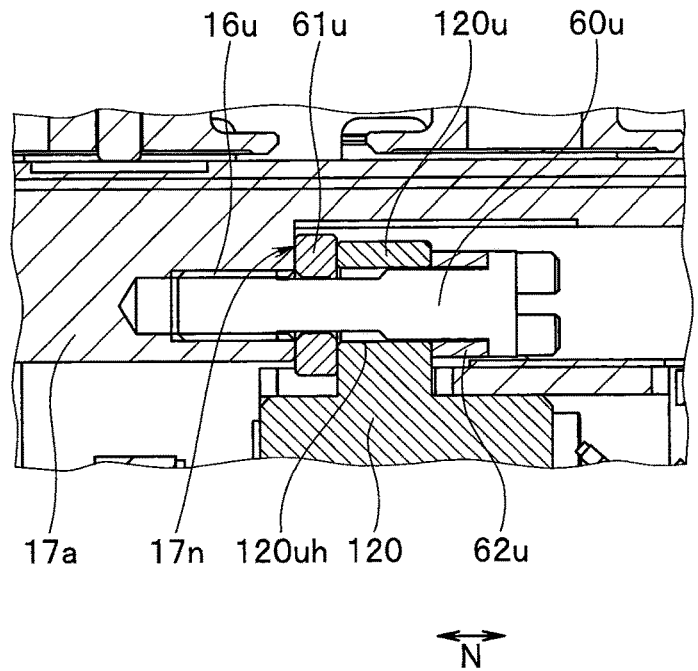
FIG. 6 is a partial cross-sectional view showing, in an enlarged manner, an upper-side fixing portion of a fixing frame in FIG. 3.

Next, a configuration for fixing the internal unit 150 to the inner surface 17*n* of the main cover 17*a* of the exterior member 17 will be described with reference to FIGS. 3 to 5, and FIGS. 6 and 7. FIG. 6 is a partial cross-sectional view showing, in an enlarged manner, the upper-side fixing portion of the fixing frame in FIG. 3, and FIG. 7 is a partial cross-sectional view showing, in an enlarged manner, the lower-side fixing portion of the fixing frame in FIGS. 4 and 5.

As described above, the internal unit 150 is provided in the internal portion 17*i* of the exterior member 17 by the upper-side fixing portion 120*u* and the lower-side fixing portions 120*r*, 120*l* of the fixing frame 120 being fixed to the inner surface 17*n* of the main cover 17*a* of the exterior member 17.

More specifically, as shown in FIGS. 3 to 6, a screw hole 16*u*, which is a fixing part, is formed at a position, of the inner surface 17*n* of the main cover 17*a* of the exterior member 17, facing the upper-side fixing portion 120*u*.

Figure 7:
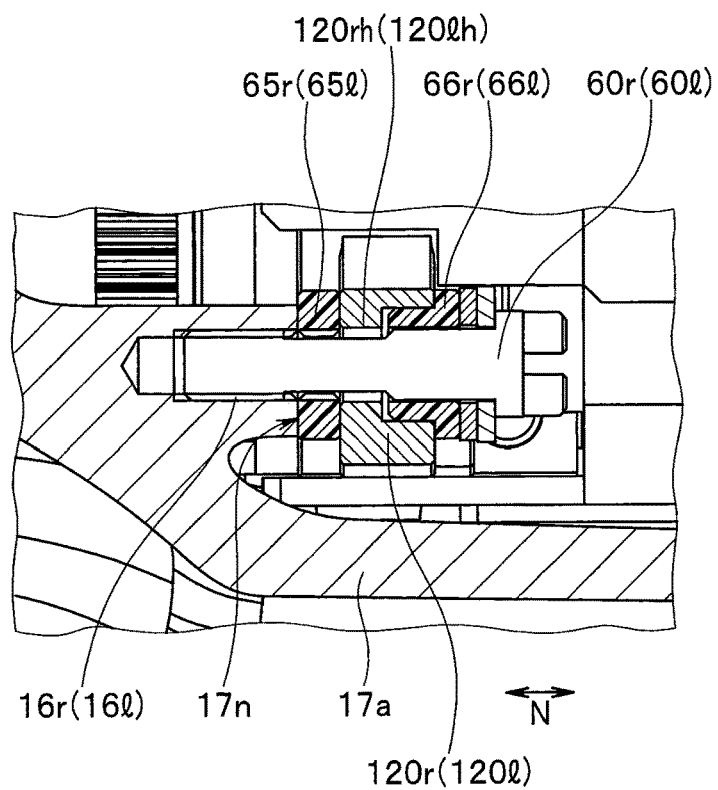
FIG. 7 is a partial cross-sectional view showing, in an enlarged manner, a lower-side fixing portion of the fixing frame in FIGS. 4 and 5.

Also, as shown in FIGS. 4, 5 and 7, screw holes 16*r*, 16*l*, which are fixing parts, are formed at positions, of the inner surface 17*n* of the main cover 17*a*, facing the lower-side fixing portions 120*r*, 120*l*.

As shown in FIG. 6, a through hole 120*uh* penetrating in the longitudinal direction N is formed to the upper-side fixing portion 120*u*.

The upper-side fixing portion 120*u* is fixed to the inner surface 17*n* via metal by a screw 60*u*, which is a fixing member inserted in the through hole 120*uh*, being screwed into the screw hole 16*u* through a metal washer 61*u* covering an outer circumference of the screw 60*u*.

Note that the metal washer 61*u* is positioned between the upper-side fixing portion 120*u* and the inner surface 17*n*.

As a result, the fixing frame 120 is connected, as shown in FIG. 3, to a region R2 of the main cover 17*a* of the exterior member 17 covered by the switch button frame 18, formed of a resin material, of the switch unit 170.

Accordingly, heat transferred from the image pickup device 33 to the fixing frame 120 is transferred via the upper-side fixing portion 120*u*, the screw 60*u*, and the metal washer 61*u* to the region R2 covered by the switch button frame 18 of the main cover 17*a* of the exterior member 17.

The switch button frame 18 prevents heat from being directly discharged outside from the upper side of the main cover 17*a*, by covering the outer circumference on the upper side of the main cover 17*a*. In other words, the switch button frame 18 prevents an operator from directly touching the upper side of the main cover 17*a*.

Furthermore, as shown in FIG. 7, through holes 120*rh*, 120*lh* penetrating in the longitudinal direction N are formed to the lower-side fixing portions 120*r*, 120*l*.

The lower-side fixing portion 120*r*, 120*l* is fixed to the inner surface 17*n* via a washer 65*r*, 65*l* and a bush 66*r*, 66*l*, which are heat insulating members covering an outer circumference of a screw 60*r*, 60*l*, which is a fixing member inserted into the through hole 120*rh*, 120*lh*, by the screw 60*r*, 60*l* being screwed into the screw hole 16*r*, 16*l* through the washer 65*r*, 65*l* and the bush 66*r*, 66*l*.

Note that the washers 65r, 65l and the bushes 66r, 66l are formed of members with a lower thermal conductivity than metal.

Also, the washer 65r, 65l is positioned between the lower-side fixing portion 120r, 120l and the inner surface 17n.

That is, the lower-side fixing portions 120r, 120l formed of metal do not come into direct contact with the inner surface 17n of the main cover 17a formed of metal.

The washers 65r, 65l and the bushes 66r, 66l are formed of members with a lower thermal conductivity than metal, and are members configured to prevent the screw holes 16r, 16l of the main cover 17a and the surroundings of the screw holes from being locally heated due to heat transferred from the image pickup device 33 to the fixing frame 120 being transferred to the main cover 17a of the exterior member 17 via the lower-side fixing portions 120r, 120l.

Note that if a screw groove is formed to an inner circumferential surface of the washer 65r, 65l, the washer 65r, 65l is screwed with an outer circumference of the screw 60r, 60l when the washer 65r, 65l covers the outer circumference of the screw 60r, 60l, and thus, the washer 65r, 65l may be prevented from falling off.

Note that other configurations of the camera head 3 are well known, and description of such configurations is omitted.

As described above, according to the configuration of the present embodiment where the internal unit 150 is fixed to the screw holes 16u, 16r, 16l of the inner surface 17n of the exterior member 17 by using the screws 60u, 60r, 60l, the lower-side fixing portions 120r, 120l of the fixing frame 120 are fixed to the inner surface 17n via the washers 65r, 65l and the bushes 66r, 66l by the screws 60r, 60l being screwed into the screw holes 16r, 16l through the washers 65r, 65l and the bushes 66r, 66l.

That is, the lower-side fixing portions 120r, 120l are indicated to not come into direct contact with the main cover 17a.

Also, the internal unit 150 is indicated to be fixed to the inner surface 17n of the exterior member 17 without being in contact except at the upper-side fixing portion 120u, the lower-side fixing portions 120r, 120l, and the heat dissipation sheet 140.

Accordingly, heat transferred from the image pickup device 33 to the fixing frame 120 may be prevented by the washers 65r, 65l and the bushes 66r, 66l, which are heat insulating members formed of resin material, from being transferred from the lower-side fixing portions 120r, 120l to parts of the main cover 17a where the screw holes 16r, 16l are formed.

That is, it may prevent the screw holes 16r, 16l of the main cover 17a and the surroundings of the screw holes which are possibly touched by an operator from being locally heated.

The present embodiment also indicates that heat transferred from the image pickup device 33 to the fixing frame 120 is transferred to the metal provided in regions R1, R2 connected to the fixing frame 120 and covered with resin materials.

More specifically, the heat dissipation plate 110 extending to the region R1 is connected to the fixing frame 120, and heat transferred from the image pickup device 33 to the fixing frame 120 is transferred to the heat sink 130 via the heat dissipation plate 110, the heat dissipation sheet 140, and the rear cover 17b, and is then transferred to the conductor of the camera cable 12 via the cable fixing frame 41. That is, the heat is indicated to be transferred to the region R1 covered by the exterior cover 40, and to be then transferred to the camera cable 12.

Moreover, the region R2, of the main cover 17a of the exterior member 17, covered by the switch button frame 18 is connected to the upper-side fixing portion 120u of the fixing frame 120, and heat transferred from the image pickup device 33 to the fixing frame 120 is indicated to be transferred to the region R2, of the main cover 17a of the exterior member 17, covered by the switch button frame 18 via the upper-side fixing portion 120u, the screw 60u, and the metal washer 61u.

Accordingly, heat from the image pickup device 33, that is, heat from the internal portion 17i of the exterior member 17, is dissipated to the metal at the regions R1, R2 which are not touched by an operator, and heat is not easily transferred to metal parts of the camera head 3 which are directly touched by the operator.

Accordingly, the temperature of the internal portion 17i of the exterior member 17 may be reduced, and also, even when the exterior member 17 is formed of metal, the temperature of the part of the exterior member 17 and other parts of the camera head where an operator touches may be reduced.

The camera head 3 having a configuration according to which the fixing parts of the internal unit 150 of the one-layer exterior member 17 serving also as an airtight case can be prevented from being locally heated by heat from the image pickup unit 100 in the internal portion 17i of the exterior member 17 may thus be provided.

Figure 8:
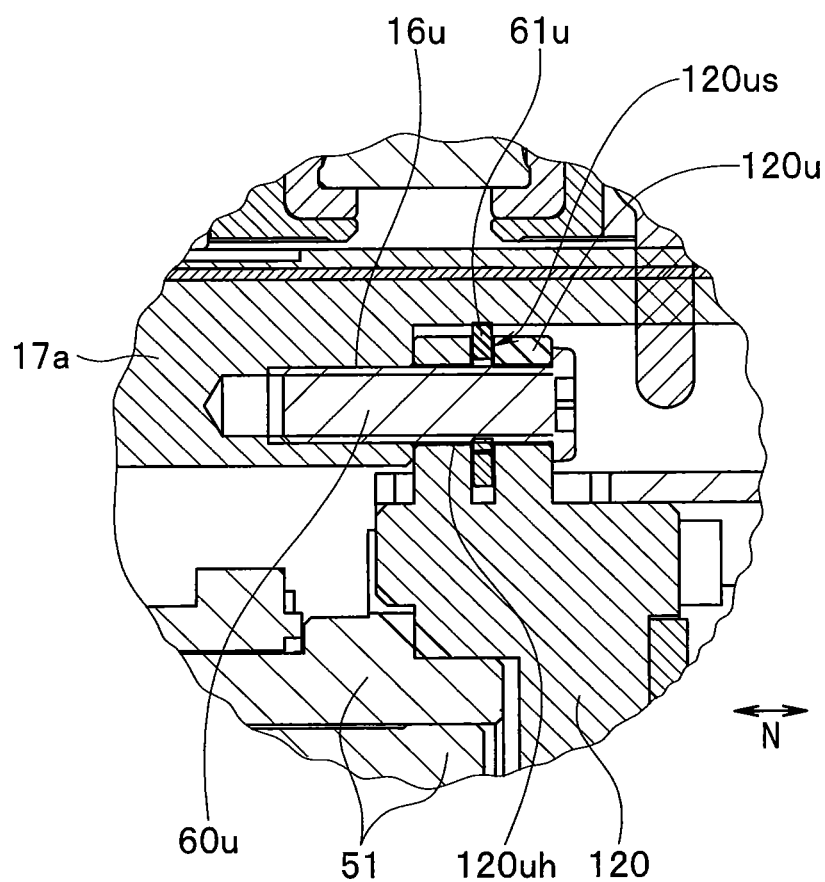
FIG. 8 is a partial cross-sectional view showing a modification of a shape of the upper-side fixing portion of the fixing frame in FIG. 6.

Note that a modification will be described below with reference to FIG. 8. FIG. 8 is a partial cross-sectional view showing a modification of a shape of the upper-side fixing portion of the fixing frame in FIG. 6.

Now, to prevent breakage of structural components of the internal unit 150 at the time of fixation of the internal unit 150 to the inner surface 17n of the exterior member 17, and to increase the optical accuracy of the lenses 30, a structure allowing the internal unit 150 to be fixed with the highest possible positioning accuracy is desired.

More specifically, the internal unit 150 is preferably fixed to the inner surface 17n of the exterior member 17 at the position of the center of gravity of the internal unit 150.

The internal unit 150 is preferably fixed at the position of the center of gravity of the internal unit 150 when taking into account optical eccentricity of the lenses 30 and the like that is caused by breakage, deformation or the like of the fixing parts of the internal unit 150 in the exterior member 17 caused at the time of application of load such as impact or vibration on the camera head 3.

However, as described above, if the internal unit 150 is fixed at the position of the center of gravity while configuring the exterior member 17 by one layer, the positions in the longitudinal direction N of the screw holes 16u, 16r, 16l where the fixing parts for the internal unit 150 in the exterior member 17, that is, the screws 60u, 60r, 60l for fixing the internal unit 150, are screwed are separated from the proximal end of the main cover 17a in the forward direction.

As a result, a problem that a task of screwing the screws 60u, 60r, 60l by using a tool such as a screwdriver, that is, a task of assembling the camera head 3, becomes difficult is caused.

More specifically, for example, a task of placing the internal unit 150 inside from an opening on the proximal end of the main cover 17a, causing each fixing portion 120u, 120r, 120l to abut the fixing part of the main cover 17a, and then screwing the screw 60u, 60r, 60l into the screw hole 16*u*, 16*r*, 16*l* through the through hole 120*uh*, 120*rh*, 120*lh* formed to respective fixing portion 120*u*, 120*r*, 120*l* by using a tool such as a screwdriver becomes difficult, possibly causing the screw 60*u*, 60*r*, 60*l* to fall out.

A configuration is conceivable according to which the screws 60*u*, 60*r*, 60*l* are inserted through the through holes 120*uh*, 120*rh*, 120*lh* in advance and the outer circumferences of the screws 60*u*, 60*r*, 60*l* are covered, as described above, by the washers 61*u*, 61*r*, 61*l* for preventing falling so that the screws 60*u*, 60*r*, 60*l* are prevented from falling out of the through holes 120*uh*, 120*rh*, 120*lh* in the longitudinal direction N.

However, according to the configuration, because the washers 61*u*, 61*r*, 61*l* abut against the fixing parts of the inner surface 17*n* of the exterior member 17, as shown in FIGS. 5 and 6, abutting positioning accuracy of the internal unit 150 is possibly reduced, thereby possibly resulting in optical eccentricity of the lenses 30 of the internal unit 150 after fixation.

Accordingly, as shown in FIG. 8, a configuration is conceivable according to which a slot 120*us* is provided at a substantially center position of the upper-side fixing portion 120*u* in the longitudinal direction N, and the metal washer 61*u* is provided in the slot 120*us*.

According to such a configuration, the metal washer 61*u* may prevent the screw 60*u* from falling out, as in a conventional case, and also, the upper-side fixing portion 120*u* comes into direct contact with the fixing part of the inner surface 17*n* of the exterior member 17. Accordingly, the internal unit 150 may be fixed with high positioning accuracy, and also, the ease of assembly of the camera head 3 is increased.

Note that the configuration described above cannot be applied to the lower-side fixing portions 120*r*, 120*l*. The reason is that if the lower-side fixing portions 120*r*, 120*l*, which are formed of metal, come into direct contact with the exterior member 17, heat is transferred, thereby causing the fixing parts of the exterior member 17 to be locally heated.

Moreover, if a screw 60*u* having a length by which a head of the screw 60*u* is positioned near the proximal end of the main cover 17*a*, the task of screwing the screw 60*u* into the screw hole 16*u* by using a tool such as a screwdriver is facilitated, and also, diffusion of heat, transferred to the screw 60*u*, from the screw 60*u* may be increased.

Furthermore, if the screw 60*u* is formed of a material having a high thermal conductivity, and the screw 60*u* is covered by a cylindrical heat dissipation material or the surface area of the head of the screw 60*u* is increased by knurling the head of the screw 60*u*, diffusion of heat, transferred to the screw 60*u*, from the screw 60*u* may be increased.

Note that in the present embodiment described above, the exterior member 17 is indicated to be formed of metal such as titanium.

The reason is that because titanium has a high strength and is light compared to other metals, if titanium is used for the exterior member, the size and the weight of the camera head 3 may be easily reduced.

However, if the image pickup unit 100 provided in the internal portion 17*i* of the main cover 17*a* of the exterior member 17 generates heat, and the heat is transferred to the main cover 17*a*, a part of the main cover 17*a* near the image pickup unit 100 is possibly locally heated.

Accordingly, the inner surface 17*n* of the main cover 17*a* may be plated with metal having a high thermal conductivity, such as gold.

In such a case, heat is diffused at the inner surface 17*n* before the heat is transferred to an outer surface of the main cover 17*a*, and it may prevent the outer surface of the main cover 17*a* from being locally increased.

Note that the inner surface 17*n* of the rear cover 17*b* may also be plated with gold. In such a case, heat of the inner surface 17*n* of the main cover 17*a* may be efficiently diffused to the inner surface 17*n* of the rear cover 17*b*. That is, heat may be discharged from the entire exterior member 17, and the exterior member 17 may be effectively prevented from being partially locally heated.

Figure 9:
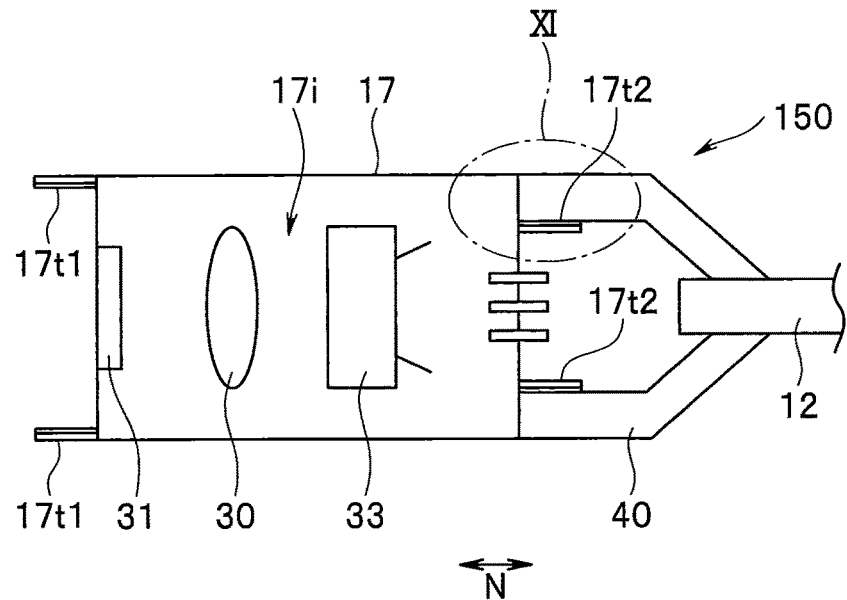
FIG. 9 is a diagram schematically showing a configuration of a modification of an exterior member of the internal unit in FIG. 3, together with an exterior cover and a camera cable.
Figure 10:
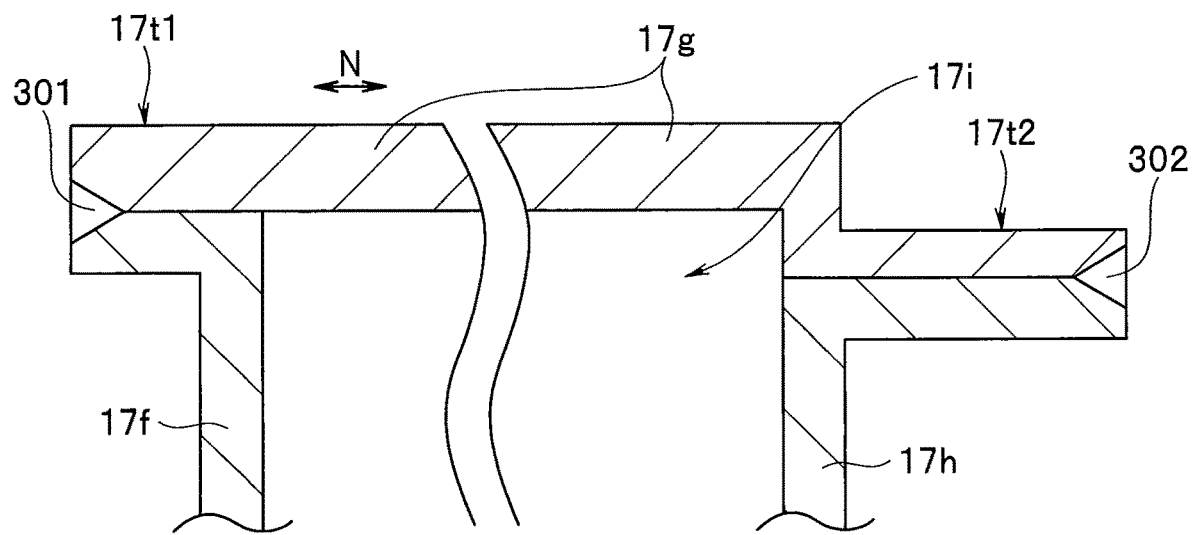
FIG. 10 is a partial cross-sectional view showing, in an enlarged manner, the exterior cover in FIG. 9.
Figure 11:
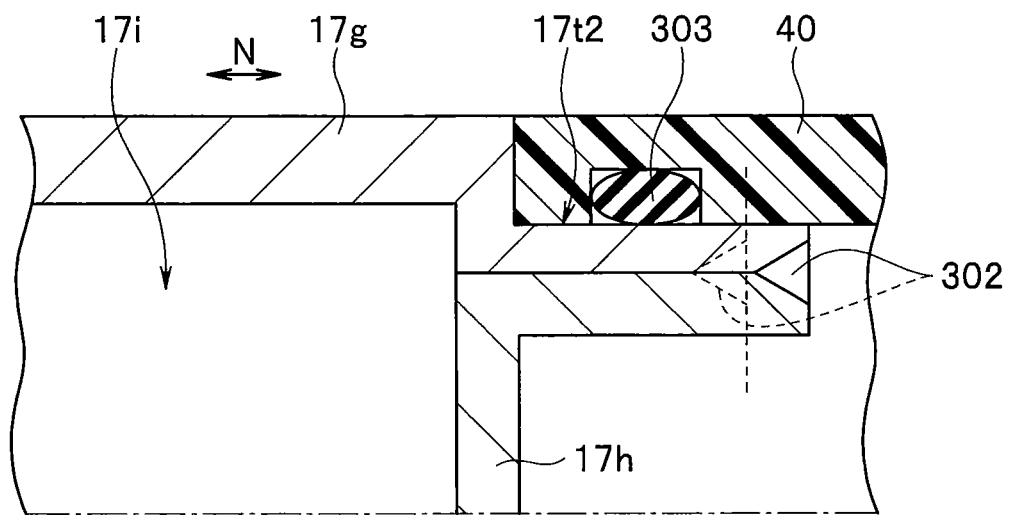
FIG. 11 is a partial cross-sectional view showing, in an enlarged manner, a part circled by line XI in FIG. 9.
Figure 12:
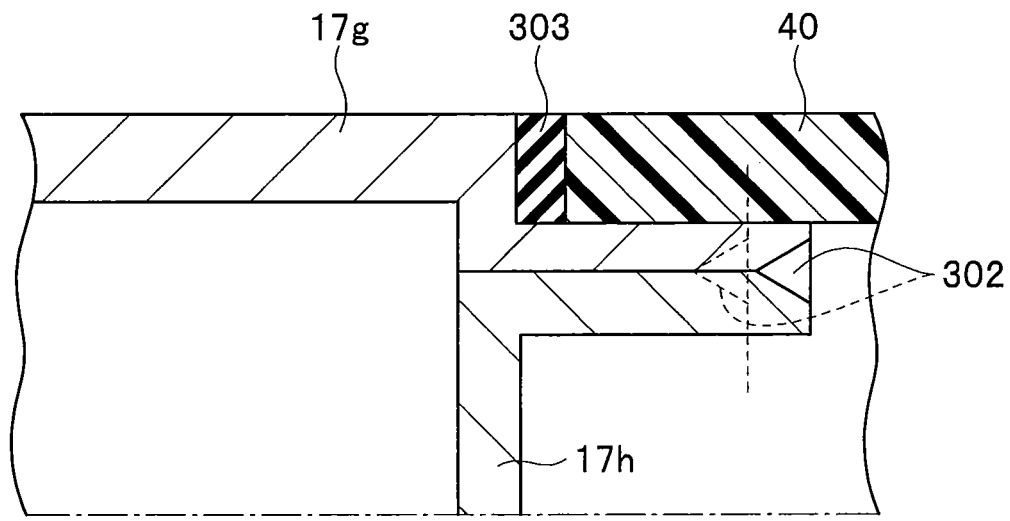
FIG. 12 is a partial cross-sectional view showing a modification of a position where a liquid-tight seal in FIG. 11 is provided.

Note that a modification will be described below with reference to FIGS. 9 to 12. FIG. 9 is a diagram schematically showing a configuration of a modification of the exterior member of the internal unit in FIG. 3, together with the exterior cover and the camera cable, FIG. 10 is a partial cross-sectional view showing, in an enlarged manner, the exterior cover in FIG. 9, FIG. 11 is a partial cross-sectional view showing, in an enlarged manner, a part circled by line XI in FIG. 9, and FIG. 12 is a partial cross-sectional view showing a modification of a position where a liquid-tight seal in FIG. 11 is provided.

When the exterior member 17 is formed of one layer and the internal unit 150 is hermetically sealed in the internal portion 17*i* as described above, the exterior member 17 has to be opened and the airtightness has to be released when a failure or the like occurs in the internal unit 150. In such a case, for example, in the case of a configuration according to which an entire outer circumference of the distal end of the rear cover 17*b* is welded to an entire outer circumference of the proximal end of the main cover 17*a*, a welded portion has to be removed across the entire circumference to perform opening.

Accordingly, the process of cutting is burdensome, and also, a problem is caused that, unless a thickness of the outer circumference of the proximal end of the main cover 17*a* is increased to provide a cutting margin, the exterior member 17 which is formed of expensive titanium cannot be reused.

Note that the same problem is caused in a configuration according to which a distal end cover, not shown, is welded and hermetically fixed to an outer circumference of the distal end of the main cover 17*a*.

To cope with such a problem, the exterior member 17 may be formed of three components including a main cover 17*g* including a forward protruding portion 17*t*1 and a rearward protruding portion 17*t*2, a distal end cover 17*f* including a forward protruding portion 17*t*1, and a rear cover 17*h* including a rearward protruding portion 17*t*2, as shown in FIGS. 9 to 11.

According to such a configuration, the distal end cover 17*f* and the distal end of the main cover 17*g* are welded and fixed together around entire circumferences of the respective forward protruding portions 17*t*1, and the rear cover 17*h* and the proximal end of the main cover 17*g* are fixed together by a welded portion 302 around entire circumferences of the respective rearward protruding portions 17*t*2.

Note that a length of each protruding portion 17*t*1, 17*t*2 in the longitudinal direction N is set to at least two times a welding depth of the welded portion 302 by laser welding.

Accordingly, for example, on the rear side of the exterior member 17, the rearward protruding portions 17*t*2 may be cut in the manner shown by a dotted line in FIG. 11 to open the exterior member 17.

As a result, because only the rearward protruding portions 17*t*2 are cut, the exterior member 17 may be easily reused several times by welding again the rearward protruding portions 17*t*2 until the rearward protruding portions 17*t*2 are no longer present.

Furthermore, because the rearward protruding portions 17*t*2 to be cut are provided at positions separated from the internal portion 17*i* of the exterior member 17, it may prevent chips from entering the internal portion 17*i*.

Note that the same thing can be said for a front side of the exterior member 17, that is, the forward protruding portions 17*t*1.

Also, although only the side of the rear cover 17*h* is shown, outer circumferences of the rearward protruding portions 17*t*2 are covered by the exterior cover 40 in a liquid-tight manner as shown in FIG. 11, and are not exposed to outside.

Furthermore, as shown in FIG. 11, the distal end of the exterior cover 40 abuts against a proximal end surface of the main cover 17*g*, and an inner circumferential surface on a distal end side of the exterior cover 40 is in contact with an outer circumferential surface of the rearward protruding portion 17*t*2 via a liquid-tight seal 303, and liquid-tightness is thus maintained.

Note that as shown in FIG. 12, the liquid-tight seal 303 may alternatively be provided between the distal end of the exterior cover 40 and the proximal end surface of the main cover 17*g*.

The external appearance of the camera head 3 is thus not changed, and also, the liquid-tightness is not affected, even when the rearward protruding portions 17*t*2 are cut to open the exterior member 17.

Figure 13:
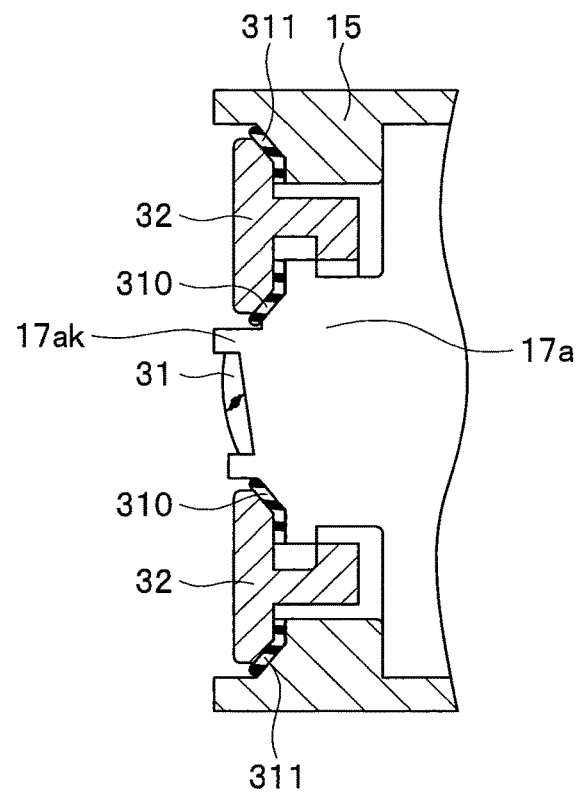
FIG. 13 is a partial cross-sectional view schematically showing, in an enlarged manner, a configuration of fixing screws for a coupler portion in FIG. 3 and a periphery of the fixing screws.

Note that a modification will be described below with reference to FIG. 13. FIG. 13 is a partial cross-sectional view schematically showing, in an enlarged manner, a configuration of fixing screws for the coupler portion in FIG. 3 and a periphery of the fixing screws.

As described above, according to a configuration where the coupler portion 15 is fixed on the distal end 17*ak* side of the main cover 17*a* by the fixing screws 32, heat of the observation window 31 fixed inside the distal end 17*ak* is easily transferred to the coupler portion 15 via the fixing screws 32.

As a result, a problem is caused that, when the eyepiece 9 of the endoscope 2 is connected to the coupler portion 15, the observation window 31 tends to be clouded due to the heat from the coupler portion 15.

Also, when liquid-tight O-shaped rings are used at front and rear of the fixing screws 32, a problem is caused that a contact area between the fixing screws 32 and the distal end 17*ak* side of the main cover 17*a* is increased and that an outer shape is complicated.

In view of such problems, to maintain liquid-tightness, heat insulating rubber sheets 310 may be provided between the outer circumference on the distal end 17*ak* side of the main cover 17*a* and inner circumferences of the fixing screws 32, and heat insulating rubber sheets 311 may be provided between outer circumferences of the fixing screws 32 and an inner circumference of the coupler portion 15, as shown in FIG. 13.

According to such a configuration, a contact area between the distal end 17*ak* and the fixing screws 32 is reduced by the rubber sheets 310, and also, heat transfer to the coupler portion 15 side is reduced due to the heat insulating effect of the rubber sheets 310.

Accordingly, the observation window 31 becomes difficult to be clouded when the eyepiece 9 is connected to the coupler portion 15.

Furthermore, due to a simple configuration of simply interposing the rubber sheets 310, 311, the external appearance is also simplified, and the readiness of cleaning and disinfection is also enhanced.

Note that the fixing screws 32 may be formed of a material with a low thermal conductivity, such as titanium or resin. Heat conductivity through the fixing screws 32 is thereby reduced, and it may further prevent the observation window 31 from being clouded.

As shown in FIG. 3 described above, various substrates that are retained by the substrate holder 200, which is bent into an L shape, and that are electrically connected to the image pickup device 33 are provided in the internal portion 17*i* of the exterior member 17, behind the image pickup device 33.

The substrate holder 200 here has to be formed of a resin material which is heat-resistant to high-temperature high-pressure steam in the autoclave process. Resin materials having heat resistance are limited, and Teflon (registered mark) and Radel (registered mark) may be cited, for example.

However, Teflon (registered mark) is heat resistant and has bendability but is poor in formability, and Radel (registered mark) is heat resistant but is hard and is not easily bent and formed into an L shape.

In view of such a problem, the substrate holder 200 may be formed of two components, and the substrate holder 200 may be formed into an L shape by hinging end portions of the respective components.

According to such a configuration, a resin material with heat resistance may be used for the substrate holder 200 without considering bendability nor formability, and thus, the cost can be reduced, and also, the resin material can be selected from a wide range of options.

As described above, according to the present embodiment, the exterior member 17 is formed of titanium.

However, although a titanium surface is normally covered with a stable oxide film and is not easily discolored, if chemical polishing or blasting is applied to an outer surface to improve the external appearance, the oxide film becomes unstable, and a problem is caused that the surface tends to be discolored after the autoclave process.

In view of such a problem, a material that promotes oxidation (such as alumina) may be used on the outer surface of the titanium exterior member 17, and blasting may be performed using small shape media ($\varphi$ 45 μm to 53 μm), and a stable oxide film may be formed by blasts remaining on the outer surface.

However, the external appearance does not change in such a state, and thus, blasting may be performed on the outer surface of the exterior member 17 using large shape media ($\varphi$ 125 μm to 250 μm) by using zirconia (glass may also be used) or the like so as to improve the external appearance by suppressing glossiness.

As described above, a stable oxide film may be formed on the outer surface of the titanium exterior member 17, and also, the quality of the external appearance may be increased, and discoloration of the external appearance after the autoclave process may be prevented.

Figure 14:
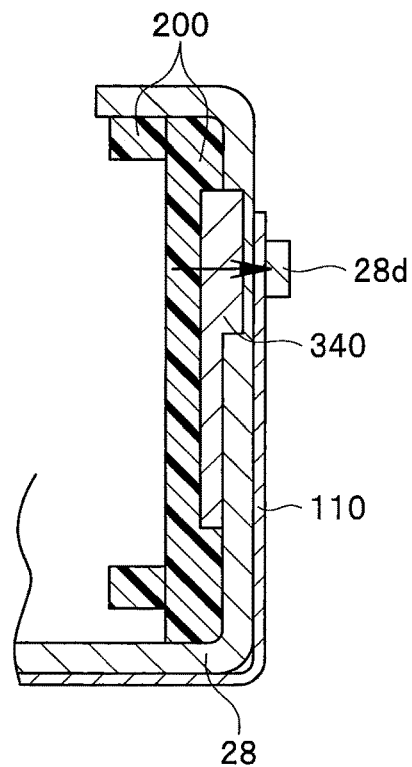
FIG. 14 is a diagram schematically showing a cross-section of the internal unit taken along line XIV-XIV in FIG. 5.

Note that a modification will be described below with reference to FIG. 14. FIG. 14 is a diagram schematically showing a cross-section of the internal unit taken along line XIV-XIV in FIG. 5.

Normally, the heat dissipation plate 110 of the internal unit 150 is fixed to the frame 28 by using a plurality of screws, but a structure allowing reduction of screw fixing parts in number is desired.

Accordingly, as shown in FIGS. 5 and 14, a configuration is possible where a protruding portion 28d, which is a part of the frame 28 protruding outward, may be formed, and a part of the heat dissipation plate 110 may be slid and be engaged inside the protruding portion 28d so as to eliminate one screw fixing part of the heat dissipation plate 110.

Also, as shown in FIG. 14, by providing an elastic heat dissipation sheet 340 between the substrate holder 200 and the frame 28, a part of the heat dissipation plate 110 is pressed against and engaged with the protruding portion 28d by the elasticity of the heat dissipation sheet 340. Accordingly, it may prevent the part of the heat dissipation plate 110 from being falling out from the protruding portion 28d.

Also, a substrate that is retained in the substrate holder 200 generates heat, but the heat is reliably transferred to the heat dissipation plate 110 via the heat dissipation sheet 340 in contact with the substrate holder 200, and thus, heat dissipation may be enhanced with respect to heat from a substrate retained in the substrate holder 200.

As described above with reference to FIG. 3, the flexible substrate 38 is bent into a U shape, and the connector 38b at an end portion is electrically connected to the substrate 320. Accordingly, the flexible substrate 38 is compactly arranged inside the rear cover 17b.

However, according to such a configuration, it is difficult to secure a space for arranging a heat insulating sheet that prevents the flexible substrate 38 from coming into contact with the conductive pins 42.

Accordingly, as shown in FIG. 3, instead of the heat insulating sheet, a reinforcement sheet 38h of polyimide may be provided at a part, of the flexible substrate 38, facing the conductive pins 42.

According to such a configuration, heat insulation between the flexible substrate 38 and the conductive pins 42 may be reliably secured by the reinforcement sheet 38h while miniaturizing the camera head 3.

What is claimed is:

1. An image pickup apparatus detachably connected to an endoscope, the image pickup apparatus comprising:
   an exterior member configured to maintain an internal portion in an airtight manner, the exterior member being formed of one-layer metal;
   a coupler fixed to an outer circumference on a distal end of the exterior member, the coupler being configured for detachably connecting to the endoscope;
   an internal unit provided in the internal portion of the exterior member, the internal unit including a heat generating element;
   a metallic retaining member provided in the internal unit, the metallic retaining member including at least one fixing portion configured to retain the internal unit and to fix the internal unit to an inner surface of the exterior member; and
   a heat insulating member provided between the at least one fixing portion of the retaining member and a fixing part of the inner surface of the exterior member, the heat insulating member being formed of a material with a lower thermal conductivity than the one-layer metal of the exterior member, wherein
   the at least one fixing portion of the metallic retaining member is fixed to the fixing part of the exterior member by a fixing member via the heat insulating member, and
   the heat insulating member covers an outer circumference of the fixing member.

2. An image pickup apparatus detachably connected to an endoscope, the image pickup apparatus comprising:
   an exterior member configured to maintain an internal portion in an airtight manner, the exterior member being formed of one-layer metal;
   a coupler fixed to an outer circumference on a distal end of the exterior member, the coupler being configured for detachably connecting to the endoscope;
   an internal unit provided in the internal portion of the exterior member, the internal unit including a heat generating element;
   a metallic retaining member provided in the internal unit, the metallic retaining member including at least one fixing portion configured to retain the internal unit and to fix the internal unit to an inner surface of the exterior member; and
   a heat insulating member provided between the at least one fixing portion of the retaining member and a fixing part of the inner surface of the exterior member, the heat insulating member being formed of a material with a lower thermal conductivity than the one-layer metal of the exterior member, wherein
   the metallic retaining member is configured such that a part of the metallic retaining member is connected to the one-layer metal provided in a region covered by the heat insulating member with a lower thermal conductivity than the one-layer metal.

3. The image pickup apparatus for an endoscope according to claim 2, wherein
   the exterior member is configured such that a part of the exterior member is covered by the heat insulating member with a lower thermal conductivity than the one-layer metal, and the fixing portion of the retaining member is provided in plurality, and
   among the fixing portion in plurality, the fixing portion facing a portion, of the exterior member, covered by the heat insulating member with a lower thermal conductivity than the one-layer metal is in contact with and connected to the fixing part of the exterior member.

4. The image pickup apparatus for an endoscope according to claim 3, wherein the exterior member is configured such that a part of the exterior member is covered by a switch unit that includes the heat insulating member with a lower thermal conductivity than the one-layer metal and is used for an image pickup operation.

5. The image pickup apparatus for an endoscope according to claim 2, wherein
   the exterior member is configured such that an outer circumference on an end portion side is covered by the heat insulating member with a lower thermal conductivity than the one-layer metal, and
   an inner-exterior member heat transfer member formed of metal and extending into the end portion of the exterior member is connected to the metallic retaining member.

6. The image pickup apparatus for an endoscope according to claim 5, wherein a pipe sleeve formed of metal, an outer circumference of which is covered by the heat insulating member with a lower thermal conductivity than the one-layer metal, is connected to the end portion of the exterior member via an outer-exterior member heat transfer member formed of metal.

7. The image pickup apparatus for an endoscope according to claim 2, wherein a cable section including, on an inside, a metal conductor, an outer circumference of which is covered by the heat insulating member with a lower thermal conductivity than the one-layer metal, is connected to the pipe sleeve.

8. The image pickup apparatus for an endoscope according to claim 2, wherein the heat generating element is an image pickup unit including an image pickup device.

9. The image pickup apparatus for an endoscope according to claim 2, wherein the heat insulating member with a lower thermal conductivity than the one-layer metal is a resin material.

10. The image pickup apparatus for an endoscope according to claim 5, wherein
- the metal provided in the region covered by the heat insulating member with a lower thermal conductivity includes a heat dissipation sheet and a rear cover, and
- the heat dissipation sheet is provided on a proximal end surface of the inner-exterior member heat transfer member, and is in surface contact with an inner surface of the rear cover in a state of being squashed by the inner surface.

11. An endoscope system comprising:
an endoscope, and
the image pickup apparatus according to claim 1, detachably connected to the endoscope.

12. An endoscope system comprising:
an endoscope, and
the image pickup apparatus according to claim 2, detachably connected to the endoscope.

* * * * *